United States Patent
Schoeberl (10) Patent No.: US 9,188,523 B2
(45) Date of Patent: Nov. 17, 2015

(54) SYSTEM FOR ESTIMATING SIZE DISTRIBUTION AND CONCENTRATION OF AEROSOLS IN ATMOSPHERIC REGION

(71) Applicant: Mark R Schoeberl, Silver Spring, MD (US)

(72) Inventor: Mark R Schoeberl, Silver Spring, MD (US)

(73) Assignee: SCIENCE AND TECHNOLOGY CORPORATION, Hampton, VA (US)

( * ) Notice: Subject to any disclaimer, the term of this patent is extended or adjusted under 35 U.S.C. 154(b) by 292 days.

(21) Appl. No.: 13/871,523

(22) Filed: Apr. 26, 2013

(65) Prior Publication Data

US 2014/0320639 A1    Oct. 30, 2014

(51) Int. Cl.
*H04N 7/18*  (2006.01)
*G01N 15/02*  (2006.01)

(52) U.S. Cl.
CPC ................................. *G01N 15/0205* (2013.01)

(58) Field of Classification Search
CPC .......... G01N 15/0227; G01N 15/0205; G01N 21/55; G01N 21/65; G01N 21/538; G01S 17/95; G01S 17/88; G01S 17/89; G01J 3/443; G01J 3/44
See application file for complete search history.

(56) References Cited

U.S. PATENT DOCUMENTS

| | | | | |
|---|---|---|---|---|
| 3,841,763 | A * | 10/1974 | Lewis | 356/438 |
| 3,931,462 | A * | 1/1976 | Exton | 348/162 |
| 5,257,085 | A * | 10/1993 | Ulich et al. | 356/73 |
| 6,597,799 | B1 * | 7/2003 | Pfaff et al. | 382/100 |
| 7,495,767 | B2 * | 2/2009 | Kim et al. | 356/438 |
| 7,872,584 | B2 * | 1/2011 | Chen | 340/628 |
| 2004/0130702 | A1* | 7/2004 | Jupp et al. | 356/5.01 |
| 2007/0046448 | A1* | 3/2007 | Smitherman | 340/431 |
| 2008/0046217 | A1* | 2/2008 | Polonskiy et al. | 702/179 |
| 2010/0235095 | A1* | 9/2010 | Smitherman | 701/208 |
| 2014/0004559 | A1* | 1/2014 | Hill et al. | 435/34 |

OTHER PUBLICATIONS

Roy G. Grainger et al., "Calculation of Mie derivatives," Applied Optics, vol. 43, No. 28, Oct. 2004, pp. 5386-5393.

* cited by examiner

*Primary Examiner* — Victor Kostak
(74) *Attorney, Agent, or Firm* — Peter J. Van Bergen (57) ABSTRACT

A system for estimating size distribution and concentration of aerosols in an atmospheric region includes a digital camera, a sunlight attenuation filter, and a processor. The filter is aligned between the sun and the camera's aperture. Image processing is performed on an image captured when the filter and the sky are in focus of the camera. The image includes (i) sunlight passing through the filter, and (ii) sunlight scattered by the atmosphere and not incident on the filter. The image processing compares intensity of a first portion of the image defined by the sunlight so-scattered to Mie and Rayleigh scattering computations generated for aerosols of known size distributions where a closest match is indicative of size distribution of aerosols. The image processing determines total solar irradiance in a second portion of the image defined by the sunlight so-passed through the filter as an indication of total concentration of aerosols.

14 Claims, 6 Drawing Sheets

SYSTEM FOR ESTIMATING SIZE DISTRIBUTION AND CONCENTRATION OF AEROSOLS IN ATMOSPHERIC REGION

FIELD OF THE INVENTION

The invention relates generally to monitoring of atmospheric regions, and more particularly to a system for estimating the size distribution and concentration of aerosols in an atmospheric region.

BACKGROUND OF THE INVENTION

In the world of physical chemistry, aerosols are defined as systems of colloidal particles dispersed in a gas. When the gas is the Earth's atmosphere, many of the particles originate from man-made events that generate smoke, smog or dust. Human and animal populations can experience medical problems when such particles are prevalent in high concentrations. As is known in the art, larger aerosols settle/land more quickly than smaller aerosol particles that can travel for hundreds or thousands of miles. Accordingly, atmospheric science attempts to monitor local atmospheric regions as a means to monitor local aerosol generation as well as "imported" aerosols. Monitoring can be part of pollution awareness, pollution regulation, scientific research, etc.

Devices that measure aerosol concentration and size distribution include systems that draw air through a filter and then analyze material left on the filter. However, these systems are complicated and expensive. Other types of devices that can be used for aerosol measurement are photometers where the aerosol measurement process is known as sun photometry. Scientific grade photometers are designed to make direct sun measurements and measurements of the surrounding sky. The direct sun measurement can be used to make what is known as a Langley plot to determine solar intensity as an indicator of total aerosol attenuation. The sky measurement is used to determine sunlight scattering due to the presence of aerosols. Both of these measurements can be made at several discrete wavelengths using colored filters. Typical scientific-grade sun photometers are two-telescope devices (i.e., one used for direct sun measurements and one used for sky measurements) that are fairly complex and expensive. Thus, measurement of aerosol concentration and size distribution in an atmospheric region tends to be limited to well-educated and well-funded groups.

SUMMARY OF THE INVENTION

Accordingly, it is an object of the present invention to provide a system for estimating size distribution and concentration of aerosols in an atmospheric region.

Another object of the present invention is to provide a simple and inexpensive system for estimating size distribution and concentration of atmospheric aerosols.

Yet another object of the present invention is to provide a system for estimating size distribution and concentration of atmospheric aerosols that can be operated in a variety of commercial and educational settings by sophisticated and unsophisticated users.

Other objects and advantages of the present invention will become more obvious hereinafter in the specification and drawings.

In accordance with the present invention, a system is provided for estimating size distribution and concentration of aerosols in an atmospheric region. The system includes a digital camera having an image aperture, a sunlight attenuation filter, and a processor. The sunlight attenuation filter is positioned at a location that is aligned between the Earth's sun and the camera's image aperture. The processor is coupled to the digital camera and is programmed with image processing routines that are executed using a digital image captured by the digital camera when the sunlight attenuation filter and the sky of an atmospheric region are in focus of the digital camera. The digital image is thereby defined by (i) sunlight from the Earth's sun passing through the atmospheric region and subsequently passed through the sunlight attenuation filter, and (ii) sunlight from the Earth's sun scattered by the atmospheric region and not incident on the sunlight attenuation filter. The image processing performed by the processor compares intensity of a first portion of the digital image defined by the sunlight so-scattered by the atmospheric region to a plurality of Mie and Rayleigh scattering computations generated for aerosols of known size distributions. The comparison yielding the closest match is indicative of size distribution of aerosols in the atmospheric region. The image processing performed by the processor further determines total solar irradiance in a second portion of the digital image defined by the sunlight so-passed through the sunlight attenuation filter. The total solar irradiance is indicative of a total concentration of aerosols in the atmospheric region.

BRIEF DESCRIPTION OF THE DRAWINGS

Other objects, features and advantages of the present invention will become apparent upon reference to the following description of the preferred embodiments and to the drawings, wherein corresponding reference characters indicate corresponding parts throughout the several views of the drawings and wherein.

DETAILED DESCRIPTION OF THE INVENTION

Figure 1:
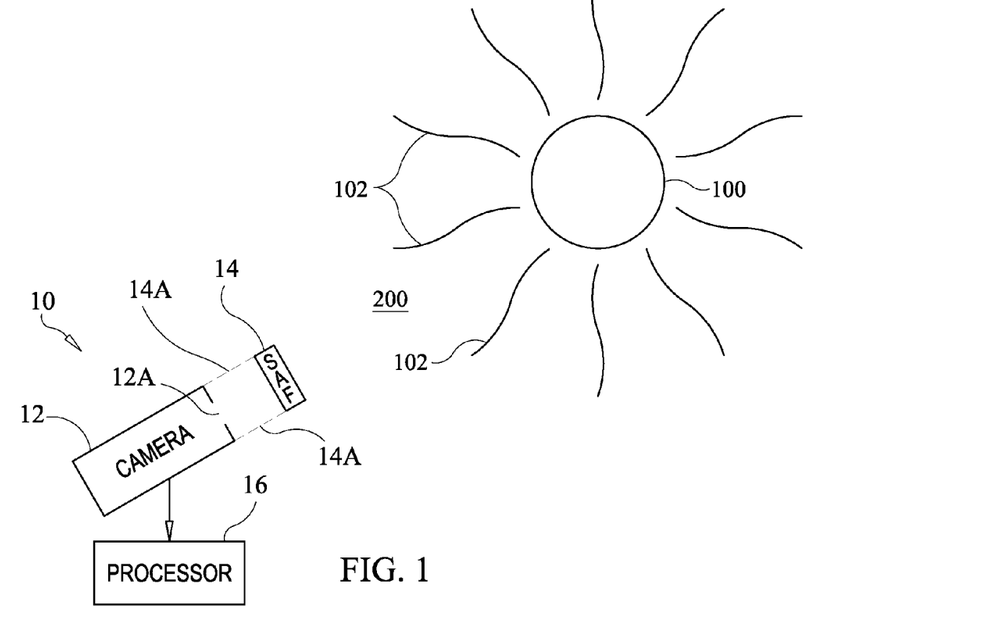
FIG. 1 is a schematic view of a system for estimating size distribution and concentration of aerosols in an atmospheric region in accordance with an embodiment of the present invention.

Referring now to the drawings and more particularly to FIG. 1, a system for estimating size distribution and concentration of aerosols in an atmospheric region (e.g., of the Earth) in accordance with an embodiment of the present invention is shown and is referenced generally by numeral 10. As is known in the art, the vast majority of aerosols reside within the first couple of kilometers of the Earth's atmosphere as measured upward from the Earth's surface (also referred to herein as the "planetary boundary layer" or PBL). Accordingly, aerosol estimations made by system 10 must take into account the zenith angle of the sun when measurement images are captured by system 10 as will be explained further below. That is, at low solar zenith angles (i.e., sun is overhead when measurement images are captured), the thickness of the aerosol layer (or PBL) "seen" by the measurement image (also known in the art as the "aerosol optical depth") is much less than at high solar zenith angles (i.e., sun is low in the sky or near the horizon).

As will be explained further below, system 10 presents a simple and inexpensive approach to achieve aerosol size distribution and concentration estimations using a single camera 12 capable of capturing a digital image, a sunlight attenuation filter ("SAF") 14, and a processor 16 for performing image processing routines that result in the estimations. While system 10 will be used to describe the operating principles of the present invention, it is to be understood that there are numerous system embodiments that can achieve these operating principles. By way of non-limiting examples, a number of alternative system embodiments will also be presented herein.

As mentioned above, camera 12 is any camera capable of capturing a digital image of a scene in focus that is passed through the aperture 12A of camera 12. Embodiments of camera 12 include, but are not limited to, stand-alone digital cameras, digital cameras incorporated in multi-function devices, digital cameras incorporated in smart phones, digital cameras incorporated in tablet-based computers, etc. Camera 12 can be mounted on a stand (not shown) to hold it steady during the digital image capture process.

Positioned between aperture 12A and the Earth's sun 100 is sunlight attenuation filter 14 that, in general, is any filter capable of attenuating (by some amount) all wavelengths of light equally. The amount of required attenuation (i.e., attenuation factor) will be dependent on the capabilities of camera 12. That is, the attenuation factor provided by filter 14 must be sufficient to prevent saturation of camera 12 while still being allowing a digital image of sun 100 to be captured through filer 14. By way of the example, filter 14 can be a neutral density filter as such filters are readily available in a variety of attenuation factors. To assure saturation-preventing attenuation of direct sunlight from sun 100, filter 14 is placed between aperture 12A and sun 100 such that a shadow (represented by the region between dashed lines 14A) cast by filter 14 falls on aperture 12A. Further and for purpose of the present invention, camera 12 is adjusted (and/or filter 14 is positioned) such that filter 14 and the sky 200 of an atmospheric region are in focus for camera 12 (i.e., filter 14 and sky 200 are in the same focal plane or depth of field).

Figure 2:
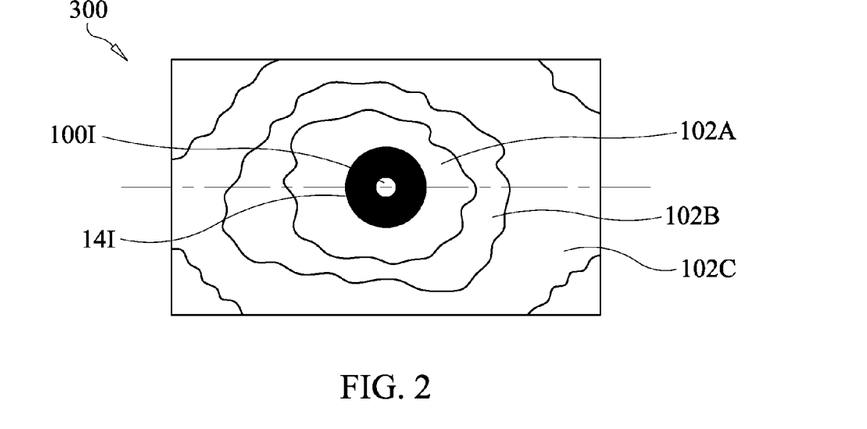
FIG. 2 is a schematic illustration of an exemplary digital image captured by the system of the present invention.

When the above-described equipment set-up conditions are satisfied, camera 12 is operated to capture a digital image. An exemplary schematic illustration of such a digital image is shown in FIG. 2 and is referenced generally by numeral 300. Digital image 300 can be in black-and-white or color without departing from the scope of the present invention since image intensity is the feature of digital image 300 that will be used during image processing. Accordingly, the various features delineated by white and black contrast in digital image 300 are representative of different image intensities in an actual digital image.

At a central region of digital image 300 is an image 100I of the Earth's sun 100. Image 100I represents the intensity of direct sunlight from sun 100 that passes through the atmospheric region and through filter 14, i.e., the amount of direct sunlight not attenuated by filter 14 but not sufficient to saturate camera 12. As sunlight from sun 100 passes through the atmosphere region being imaged, aerosols in the atmospheric region cause the sunlight to scatter where such scattered light is represented in FIG. 1 by wavy lines 102. The dark region 14I surrounding image 100I represents the portion of scattered light 102 attenuated or blocked by filter 14 in the image capture region immediately adjacent to the sun's image 100I. Accordingly, the geometric shape of dark region 14I mimics the geometric shape of filter 14. The remainder of digital image 300 represents scattered light 102 not incident on filter 14. That is, since sky 200 and filter 14 are in focus for camera 12, scattered light 102 not incident on (i.e., blocked by) filter 14 is available for capture in digital image 300. If the amount of aerosols changes in the imaged region, different regions of intensity will be defined in digital image 300. By way of example, three such regions 102A, 102B and 102C of varying scattered-light intensity are illustrated.

In accordance with the present invention, a single digital image 300 is processed by processor 16 that is programmed with image processing routines. The results of such processing are estimates of size distribution and concentration of aerosols in the atmospheric region being imaged. Additional reference will be made to FIG. 3 where the image processing approach used by the present invention is illustrated as a flow diagram. Some steps of the image processing yield an estimation of aerosol size distribution, while other steps yield an estimation of total aerosol concentration. The steps leading to the two results can be carried out in a serial or parallel processing fashion without departing from the scope of the present invention.

Figure 3:
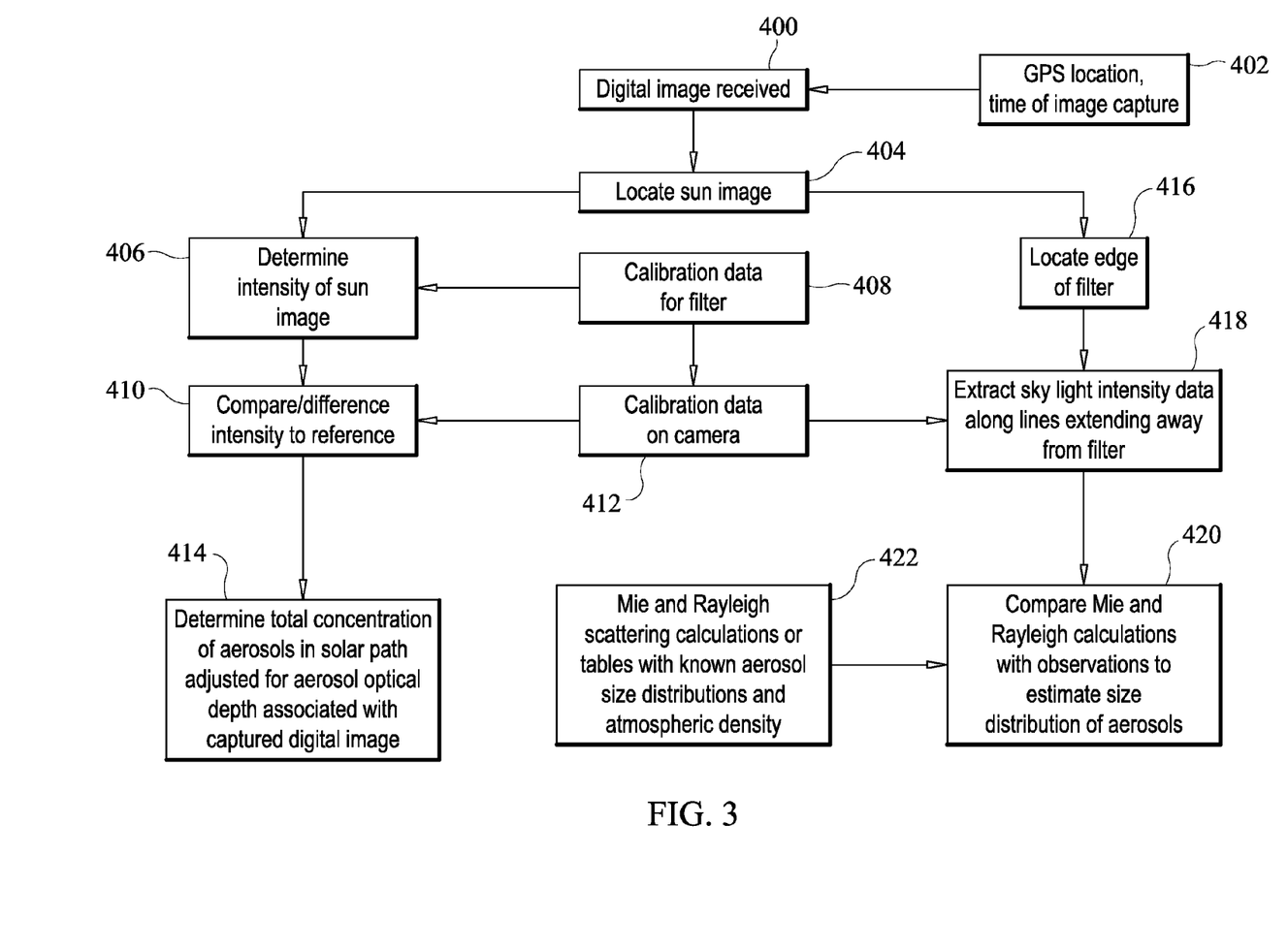
FIG. 3 is a flow diagram depicting the image processing steps employed by the system of the present invention.

Regardless of whether a serial or parallel processing approach is used, image processing commences with step 400 where a digital image (e.g., digital image 300) is received for processing. Depending on the equipment used to capture the digital image, information 402 (to include GPS location data and the time that the digital image was captured) can be included with the digital image data. Information 402 can be used to compute the solar zenith angle in accordance with techniques known in the art. The solar zenith angle can also be known or determined in other ways without departing from the scope of the present invention. The solar zenith angle is used in a Langley plot calculation as will be described later herein.

At step 404, the sun's image 100I is located in digital image 300. Depending on the system used to perform the image processing, locating sun's image 100I can be done manually (e.g., a user viewing digital image 100I identifies image 100I using a peripheral device such as a mouse, tablet pen, etc.) or automatically (e.g., the image processing identifies 100I using intensity searching techniques that can readily discern sun's image 100I from dark region 14I). Either approach can be used without departing from the scope of the present invention.

With respect to determining an estimation of the total concentration of aerosols in the atmospheric region (i.e., in the solar path between sun 100 and camera aperture 12A that is being imaged), step 406 determines the intensity of sun's image 100I as an indication of total solar irradiance along the solar path being imaged. Since sun's image 100I is a function of the attributes of filter 14, calibration data 408 associated with filter 14 can be used to "normalize" the intensity of sun's image 100I prior to further processing. Thus, the intensity of sun's image 100I is the total solar irradiance of the direct sunlight from sun 100.

Next, at step 410, the intensity from step 406 is compared/differenced with respect to a reference intensity indicative of a clear sky. For example, the intensity observed in sun's image 100I (from step 406) can be compared to (i.e., differenced with) the exo-atmosphere intensity. As is known in the art, the exo-atmosphere intensity can be determined from a Langley plot or from a calibration light source. In a Langley plot, several measurements are made through filter 14 on a clear sunny day with varying solar zenith angles. A plot of the intensity versus the secant of the zenith angle allows for extrapolation of the intensity to the exo-atmosphere for use as the reference intensity in step 410. These measurements and Langley plot calculations can be performed by the manufacturer of system 10 or by the user of system 10 without departing from the scope of the present invention.

Calibration data 412 on camera 12 can be provided/used to "normalize" the difference generated in step 410 in order to account for attributes of the specific camera used to capture the digital image being processed. The difference result from step 410 is indicative of the total concentration of aerosols in the solar path being imaged since the difference is the solar attenuation caused by the presence of aerosols relative to a clear sunny day. The difference results are provided to step 414 where the results are then adjusted in accordance with the aerosol optical depth (i.e., the solar zenith angle when the digital image was captured). That is, this adjustment scales the total concentration of aerosols in the atmospheric region predicated on the aerosol optical depth which is assumed to be concentrated in the PBL.

With respect to determining an estimation of the size distribution of aerosols in the atmospheric region being imaged, step 416 locates the outside edge of dark region 14I in digital image 300. Such location/identification can be performed manually or automatically without departing from the scope of the present invention. Next, at step 418, light intensity data is extracted from digital image 300 along regions thereof extending from the outside edge of dark region 14I. For example, such light intensity can be extracted along a horizontal region (i.e., an almucantar or locus of all points at a given solar zenith angle) of digital image 300. By way of example, the region used for the intensity extraction can be an almucantar (represented by dashed line 302) passing approximately through the center of sun's image 100I. Calibration data 412 from camera 12 can be used to "normalize" the light intensity data to account for specific camera attributes.

Next, at step 420, the extracted light intensity data from step 418 is compared to reference data 422. More specifically, reference data 422 provides Mie and Rayleigh scattering calculations (or tables of such calculations) associated with known aerosol size distribution and atmospheric density. For example, such reference data 422 can be developed using schemes disclosed by Grainger et al. in "Calculation of Mie derivatives," *Applied Optics*, Vol. 43, No. 28, pg. 5386-5393 (2004). Reference data 422 is compared (at step 420) to the intensity data from step 418 in order to find a closest match there between where the size distribution associated with the closest-match reference data 422 is indicative of the aerosol size distribution in the atmospheric region being imaged.

As mentioned above, the present invention can be realized by a variety of system constructions/configurations. Several non-limiting configurations are illustrated in FIGS. 4-7 where elements in common with system 10 are referenced with the same numerals used previously herein. While each of these embodiments illustrates a single-feature change with respect to system 10, it is to be understood the various features can be combined without departing from the scope of the present invention.

Figure 4:
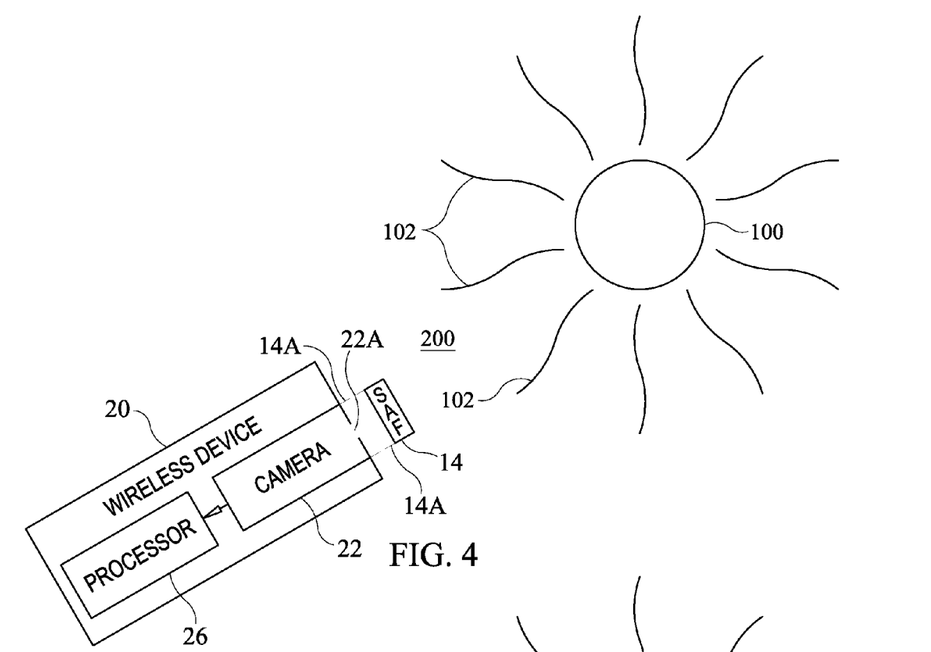
FIG. 4 is a schematic view of a system for estimating size distribution and concentration of aerosols in an atmospheric region in accordance with another embodiment of the present invention.

In FIG. 4, the functions of the above-described camera and processor are provided by a wireless device 20 having a digital camera 22 (with an image aperture 22A) incorporated therein. Device 20 can be any device capable of communicating wirelessly via a cellular or satellite network. Examples of device 20 include smart phones, tablet-based computers, etc., that generally include an on-board processor 26 for carrying out the image processing steps described above.

Figure 5:
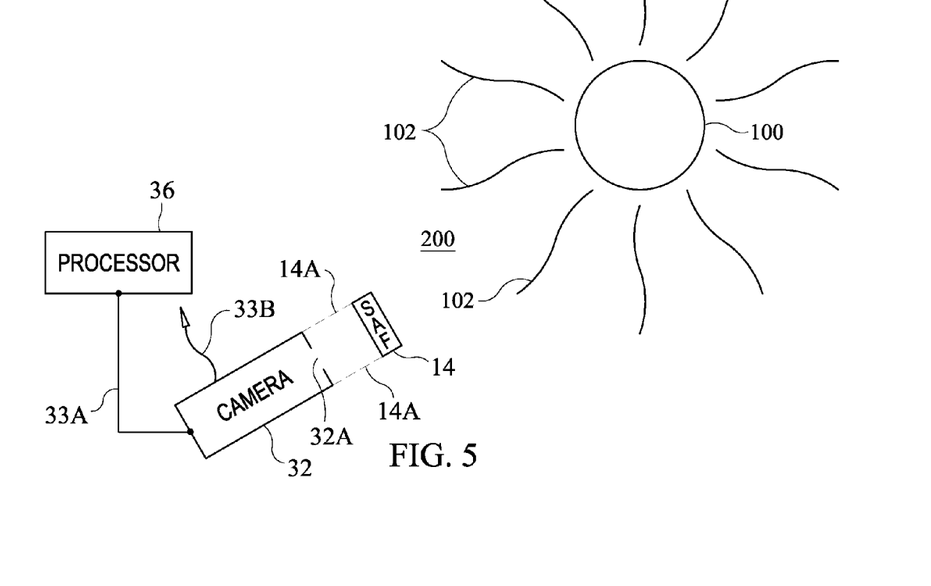
FIG. 5 is a schematic view of a system for estimating size distribution and concentration of aerosols in an atmospheric region in accordance with yet another embodiment of the present invention.

FIG. 5 illustrates another possible configuration where a camera 32 (with an image aperture 32A) does not have an on-board processor. In this configuration a processor 36 can be coupled to camera 32 via a wired connection 33A or a wireless connection 33B. That is, processor 36 can be located remotely with respect to camera 32. For example, processor 36 can be at another physical location or "in the cloud" in which case the image processing provided thereby could be offered as "software as a service". The user could then subscribe to the image processing and simply upload a captured digital image for processing in accordance with the present invention. The estimation results could be "returned" to camera 32, made available on an internet site, e-mailed to one or more addresses, texted to provided cell phone numbers, or combinations thereof.

Figures 6, 7:
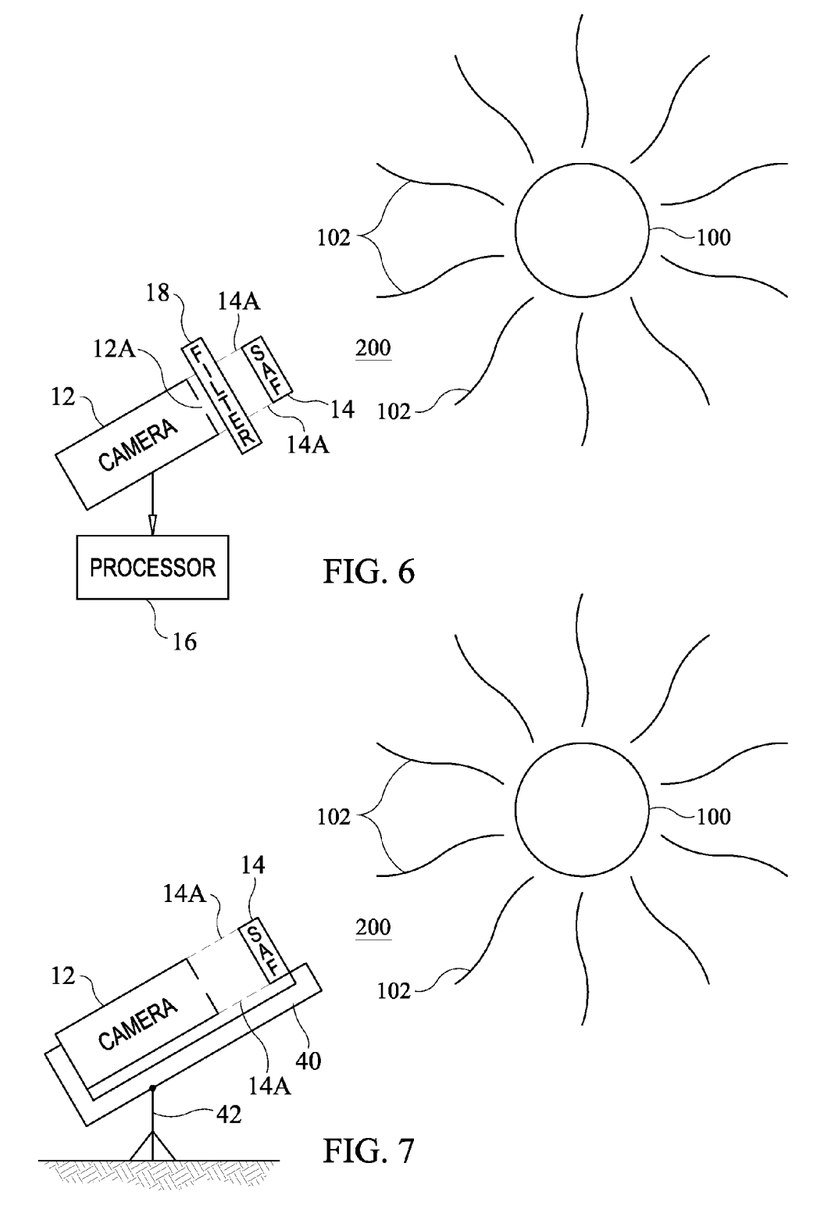
FIG. 6 is a schematic view of a system for estimating size distribution and concentration of aerosols in an atmospheric region in accordance with still another embodiment of the present invention.
FIG. 7 is a schematic view of a system for estimating size distribution and concentration of aerosols in an atmospheric region in accordance with another embodiment of the present invention in which a support structure is used to fix the relative positions of the camera and the sunlight attenuation filter.

Referring now to FIG. 6, an additional optical filter 18 can be disposed between image aperture 12A and sunlight attenuation filter 14. For example, optical filter 18 could be a color filter or a polarization filter. A color filter could be used to narrow the wavelength response of the camera for processing efficiency. Color filters could also be used to aid in identifying aerosol composition. For example, since smoke strongly absorbs blue light, a blue filter and red filter can be used in alternate image captures where differences in the total aerosol concentration using the two filters provides information on aerosol composition. A polarization filter could be used to filter Rayleigh and Mie scattered light where the filtered light/image can be used to calibrate the camera and potentially improve processing efficiency.

FIG. 7 illustrates another configuration of the present invention in which a support structure 40 is coupled camera 12 and sunlight attenuation filter 14 thereby fixing their relative positions such that filter 14 is in focus of camera 12. This simplifies system set-up as a user only needs to be sure that shadow 14A falls on image aperture 12A prior to capturing a digital image of sun 100 and sky 200. Support structure 40 can include (or be configured for coupling to) a stand 42 to hold the apparatus steady when capturing a digital image.

Figure 8:
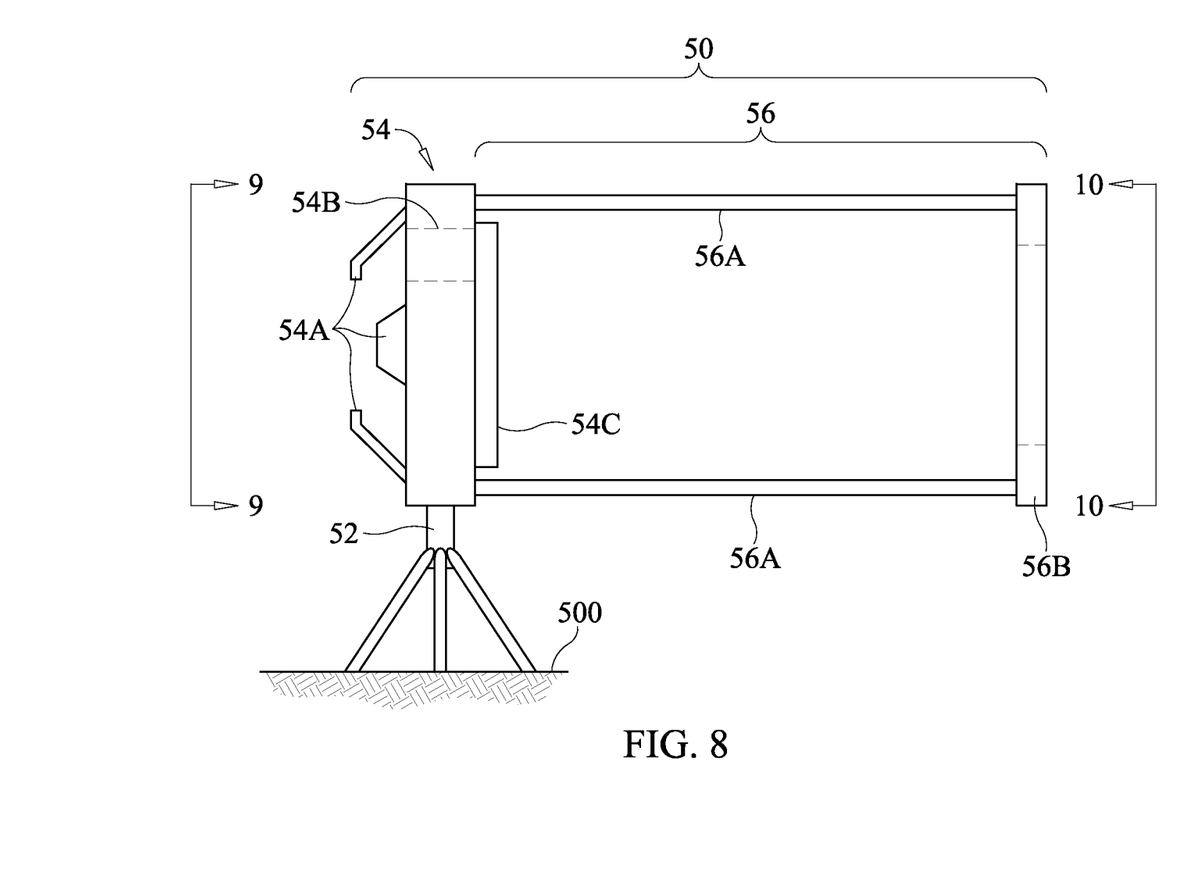
FIG. 8 is a side schematic view of a support structure for the camera and filter in accordance with an embodiment of the present invention.
Figure 9:
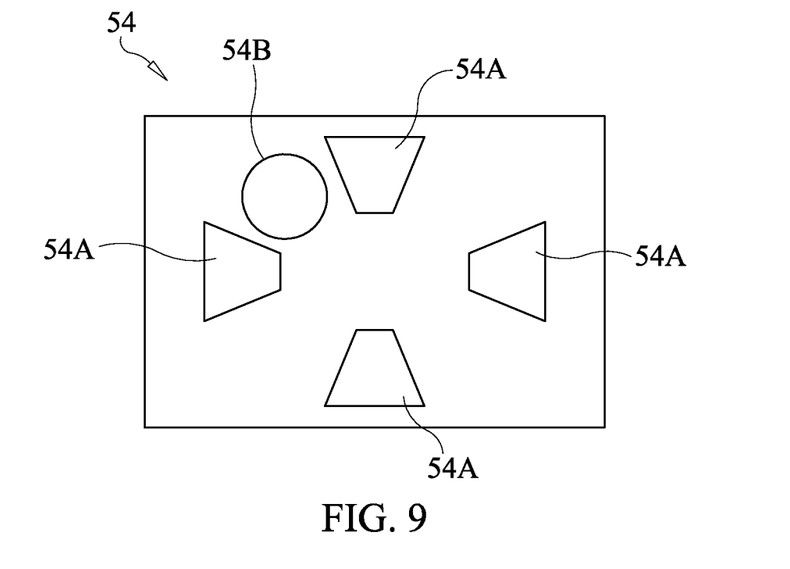
FIG. 9 is a plan view of the camera support taken along line 9-9 of FIG. 8.
Figure 10:
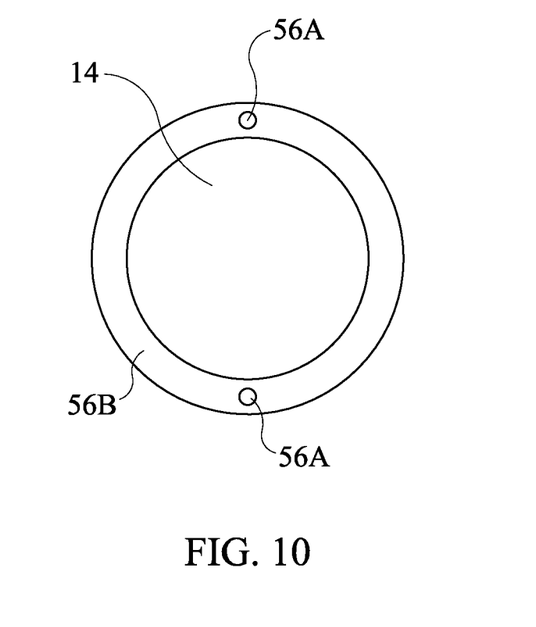
FIG. 10 is a plan view of the sunlight attenuation filter mount taken along line 10-10 in FIG. 8.

By way of non-limiting example, an embodiment of a support structure and stand will be described with simultaneous reference to FIGS. 8-10. As will be explained further below, the illustrated support structure is adaptable for use with a variety of smart phones or tablet-based computers, each of which is assumed to incorporate a digital camera, an on-board processor, and wireless communication capability. Accordingly, in FIGS. 8-10, use of the term "camera" is assumed to refer to this type of device. In FIG. 8, the support structure and stand (referenced generally by numeral 50) includes a stand 52 (e.g., a tripod), a camera support 54, and a sunlight attenuation filter support/positioner 56. Stand 52 can be any conventional (or specifically designed) stand that can be coupled to (e.g., via threads) or integrated with camera support 54. Stand 52 can be portable or fixed to some support platform 500 without departing from the scope of the present invention.

Camera support 54 can be coupled to stand 52 in such a way that camera support 54 can be rotated, pitched, etc., relative to stand 52. A variety of such "couplings" could be used as would be understood by one of ordinary skill in the art. Referring additionally to FIG. 9, camera support 54 can be a plate-like structure having a number of brackets 54A coupled to or integrated one face thereof that will hold a camera (not shown) in place. Brackets 54A can be adjustable and/or flexible to accommodate a variety of camera casings. One (or more) through hole 54B is provided so that an aperture of a camera can be aligned therewith when supported by brackets 54A. The opposing face of camera support 54 can include filter support 54C aligned with hole 54B. Filter support 54C is used to hold an optional filter (e.g., filter 18 in FIG. 6).

Sunlight attenuation filter support/positioner 56 includes one or more rigid bars/rods 56A attached on one end thereof to camera support 54 and on the other end thereof to a filter mount 56B. Bars/rods 56A can be fixed or adjustable in length without departing from the scope of the present invention. Referring additionally to FIG. 10, filter mount 56B can be a rigid ring (or ring assembly) to which the opposing ends of bars/rods 56A are coupled. Sunlight attenuation filter 14 is coupled to filter mount 56B.

The advantages of the present invention are numerous. A single digital image is image processed to provide estimations of both aerosol concentration and size distribution. The present invention is adaptable for use with the ubiquitous smart phone or tablet technology thereby allowing the present invention to be used by students, educators, scientists, industry, government regulators, etc., when making a study of aerosols in local atmospheres. Image processing could be accomplished locally or remotely thereby increasing the versatility of the present invention.

Although the invention has been described relative to a specific embodiment thereof, there are numerous variations and modifications that will be readily apparent to those skilled in the art in light of the above teachings. It is therefore to be understood that, within the scope of the appended claims, the invention may be practiced other than as specifically described.

What is claimed as new and desired to be secured by Letters Patent of the United States is:

1. A system for estimating size distribution and concentration of aerosols in an atmospheric region, comprising:
    a digital camera having an image aperture;
    a sunlight attenuation filter adapted to be positioned at a location that is aligned between the Earth's sun and said image aperture; and
    a processor coupled to said digital camera and programmed with image processing routines, said processor executing said image processing routines using a digital image captured by said digital camera when said sunlight attenuation filter and the sky of an atmospheric region are in focus of said digital camera, said digital image defined by
    (i) sunlight from the Earth's sun passing through the atmospheric region and subsequently passed through said sunlight attenuation filter, and
    (ii) sunlight from the Earth's sun scattered by the atmospheric region and not incident on said sunlight attenuation filter,
    said image processing routines comparing intensity of a first portion of said digital image defined by said sunlight so-scattered by the atmospheric region to a plurality of Mie and Rayleigh scattering computations generated for aerosols of known size distributions wherein a closest match there between is indicative of size distribution of aerosols in the atmospheric region, and
    said image processing routines further determining total solar irradiance in a second portion of said digital image defined by said sunlight so-passed through said sunlight attenuation filter wherein said total solar irradiance is indicative of a total concentration of aerosols in the atmospheric region.

2. A system as in claim 1, further comprising a support structure coupled to said digital camera and said sunlight attenuation filter for fixing said sunlight attenuation filter at said location.

3. A system as in claim 1, wherein said first portion of said digital image lies along an almucantar approximately aligned with the center of an image of the Earth's sun appearing in said digital image.

4. A system as in claim 1, wherein said second portion of said digital image comprises an image of the Earth's sun appearing in said digital image.

5. A system as in claim 1, wherein said digital camera is incorporated in a wireless device selected from the group consisting of devices that can communicate over a cellular communication system and devices that can communicate over a satellite communication system.

6. A system as in claim 1, wherein said sunlight attenuation filter comprises a neutral density filter.

7. A system as in claim 1, wherein said processor is co-located with said digital camera.

8. A system as in claim 1, wherein said processor is remotely located with respect to said digital camera.

9. A system as in claim 1, further comprising at least one additional filter disposed between said sunlight attenuation filter and said image aperture, said at least one additional filter being selected from the group consisting of a color filter and a polarization filter.

10. A system for estimating size distribution and concentration of aerosols in an atmospheric region, comprising:
    a digital camera having an image aperture;
    a neutral density filter adapted to be positioned at a location that is aligned between the Earth's sun and said image aperture wherein a shadow of said neutral density filter is cast on said image aperture;
    a support structure coupled to said digital camera and said neutral density filter for fixing said neutral density filter at said location; and
    a processor coupled to said digital camera and programmed with image processing routines, said processor executing said image processing routines using a digital image captured by said digital camera when said neutral density filter and the sky of an atmospheric region are in focus of said digital camera, said digital image defined by
    (i) sunlight from the Earth's sun passing through the atmospheric region and subsequently passed through said neutral density filter, and
    (ii) sunlight from the Earth's sun scattered by the atmospheric region and not incident on said neutral density filter,
    said image processing routines comparing intensity of a first portion of said digital image defined by said sunlight so-scattered by the atmospheric region to a plurality of Mie and Rayleigh scattering computations generated for aerosols of known size distributions wherein a closest match there between is indicative of size distribution of aerosols in the atmospheric region, wherein said first portion of said digital image lies along an almucantar approximately aligned with the center of an image of the Earth's sun appearing in said digital image, and said image processing routines further determining total solar irradiance in a second portion of said digital image defined by said sunlight so-passed through said neutral density filter wherein said total solar irradiance is indicative of a total concentration of aerosols in the atmospheric region, and wherein said second portion of said digital image comprises said image of the Earth's sun appearing in said digital image.

11. A system as in claim 10, wherein said digital camera is incorporated in a wireless device selected from the group consisting of devices that can communicate over a cellular communication system and devices that can communicate over a satellite communication system.

12. A system as in claim 10, wherein said processor is co-located with said digital camera.

13. A system as in claim 10, wherein said processor is remotely located with respect to said digital camera.

14. A system as in claim 10, further comprising at least one additional filter coupled to said support structure and disposed between said neutral density filter and said image aperture, said at least one additional filter being selected from the group consisting of a color filter and a polarization filter.

* * * * *